(12) United States Patent
Chaton et al.

(10) Patent No.: US 7,705,989 B2
(45) Date of Patent: Apr. 27, 2010

(54) MICROSENSORS AND NANOSENSORS FOR CHEMICAL AND BIOLOGICAL SPECIES WITH SURFACE PLASMONS

(75) Inventors: Patrick Chaton, Theys (FR); Jean-Louis Bijeon, Lavau (FR); Pascal Royer, Troyes (FR); Pierre Michel Adam, Sommeval (FR)

(73) Assignee: Commissariat A l'Energie Atomique, Paris (FR)

( * ) Notice: Subject to any disclaimer, the term of this patent is extended or adjusted under 35 U.S.C. 154(b) by 106 days.

(21) Appl. No.: 10/574,177

(22) PCT Filed: Oct. 7, 2004

(86) PCT No.: PCT/FR2004/050494
§ 371 (c)(1), (2), (4) Date: Mar. 30, 2006

(87) PCT Pub. No.: WO2005/033335
PCT Pub. Date: Apr. 14, 2005

(65) Prior Publication Data
US 2007/0115474 A1 May 24, 2007

(30) Foreign Application Priority Data
Oct. 9, 2003 (FR) .................................. 03 50663

(51) Int. Cl.
*G01N 21/55* (2006.01)

(52) U.S. Cl. ............................ 356/445; 356/442; 435/5; 435/7.1; 435/40.5

(58) Field of Classification Search .......... 356/442–448; 435/5, 6, 7.1, 7.32, 40.5
See application file for complete search history.

(56) References Cited

U.S. PATENT DOCUMENTS

| | | | |
|---|---|---|---|
| 5,461,600 A * | 10/1995 | Pohl | 369/44.38 |
| 5,917,607 A | 6/1999 | Naya | |
| 6,673,533 B1 * | 1/2004 | Wohlstadter et al. | 435/7.1 |
| 6,897,015 B2 * | 5/2005 | Henderson et al. | 435/5 |
| 7,088,449 B1 * | 8/2006 | Brongersma | 356/445 |
| 7,226,734 B2 * | 6/2007 | Chee et al. | 435/6 |
| 2001/0026943 A1 | 10/2001 | Dickopf et al. | |
| 2003/0027327 A1 | 2/2003 | Cunningham et al. | |
| 2004/0038307 A1 * | 2/2004 | Lee et al. | 435/7.1 |

FOREIGN PATENT DOCUMENTS

| | | |
|---|---|---|
| DE | 102 20 593 | 6/2003 |
| EP | 1 286 187 | 2/2003 |
| FR | 2 787 581 | 6/2000 |
| WO | 02/097405 | 12/2002 |

* cited by examiner

*Primary Examiner*—Gregory J Toatley, Jr.
*Assistant Examiner*—Iyabo S Alli
(74) *Attorney, Agent, or Firm*—Oblon, Spivak, McClelland, Maier & Neustadt, L.L.P.

(57) ABSTRACT

A surface plasmon microsensor or a nanosensor for chemical or biological species including pads distributed on the surface of a support, the pads including an electrically conductive material and being capable of immobilizing the chemical or biological species. The pads have a dimension less than 1 μm.

29 Claims, 3 Drawing Sheets

MICROSENSORS AND NANOSENSORS FOR CHEMICAL AND BIOLOGICAL SPECIES WITH SURFACE PLASMONS

TECHNICAL FIELD

The present invention concerns novel localised surface plasmon sensors for chemical and biological species.

STATE OF THE PRIOR ART

Surface plasmons are electromagnetic modes that propagate on a metallic conductive surface and which are the consequence of a longitudinal oscillation of the charge density due to the collective movement of electrons located on the surface of the metal. Surface plasmons may be optically excited. One thus highlights resonances that are directly linked to the various propagation modes of the surface plasmons.

Surface plasmons that may be excited are known as "delocalised" or "localised". One distinguishes them principally by their propagation length.

The most frequent uses, in the present state of the art, preferentially concern delocalised surface plasmons that propagate over distances greater than the wavelength of the exciting light, typically around 0.5 micrometer in the visible domain.

Localised surface plasmons are waves that propagate over distances less than the wavelength of the exciting light, in other words over submicronic, or even nanometric, distances.

Surface plasmons are highly sensitive to the diverse characteristics of the surrounding environment. It is thus possible to determine, for example, the physical and chemical properties of one or several molecules or nano-objects deposited on a metallic surface on which a previously excited surface plasmon propagates and thereby to form chemical and biological detectors.

Several configurations exist for exciting a delocalised surface plasmon. The most widely used configuration is that of Kretschmann. In this configuration, a first face of a prism is coated with a very thin metallic layer, in gold or in silver, intended to be brought into contact with the chemical or biological species to be detected. A reading beam is transmitted through one of the oblique faces of a total internal reflection glass prism. This beam is partially reflected on the glass/metal interface in the direction of a detector, a part of the energy of the beam being absorbed by the metal. The total reflection taking place at the metal/air interface is accompanied by the formation of an evanescent wave that excites a surface plasmon at this same interface. The excitement of the surface plasmon can only occur under certain illumination angles. When a surface plasmon is excited, the intensity of the light beam collected by the detector decreases on account of the energy transferred to the plasmon. As a function of the incidence angle of the light beam on the first face of the prism, it forms a minimum depth in the intensity of the light beam collected by the detector. This angle depends very largely on the profile of the refraction index of the metallised surface, within the thickness of the evanescent field. This refraction index changes as a function of the substances adsorbed on the metallic layer. The resonance angle, corresponding to the formation of a surface plasmon, is therefore representative of the substances adsorbed. It is also possible, at fixed incidence angle, to adapt the exciting wavelength to the plasmon resonance.

DESCRIPTION OF THE INVENTION

The present invention has been made to improve the resolution of existing sensors for chemical or biological species. It makes use of pads distributed on the surface of a support and capable of immobilising chemical or biological species. The size and the shape of the pads, as well as their distribution, may be provided so as to allow a resolution on the nanometric scale. Within the scope of the invention, localised surface plasmons are particularly used.

From a general point of view, one highlights, according to the invention, the modifications of the characteristics of the surface plasmons due to a change in the optical properties of the surrounding medium following the adsorption of chemical or biological species on the metallic substrates. Also according to the invention, the biochemical species adsorbed on the pads are identified by surface enhanced Raman spectroscopy, this enhancement and consequently this type of spectroscopy being possible thanks to the plasmon resonances of the metallic pads.

The subject of the invention is therefore a surface plasmon microsensor or a nanosensor for chemical or biological species, characterised in that it comprises pads distributed on the surface of a support, the pads comprising at least one electrically conductive material and being capable of immobilising said chemical or biological species, the pads having a dimension less than 1 µm.

Within the scope of the present invention, nanosensors are defined as being those in which the pads have a dimension less than 0.5 µm (dimension corresponding approximately to the experimental diffraction limit of an optical system) and microsensors are those in which the pads have a dimension greater than 0.5 µm.

Advantageously, the pads are distributed on the surface of the support according to a two dimensional matrix.

The pads may have a transversal section (in other words in a plane parallel to the surface of the support) in the shape of a circle or an ellipse. If the sensor is a microsensor, the section of the pads has its largest dimension between 0.5 µm and 1 µm. If the sensor is a nanosensor, the section of the pads has its largest dimension less than 0.5 µm.

The microsensor or the nanosensor may comprise at least two networks of pads, the shape of the section of the pads of one of the networks being different to the shape of the section of the pads of the other network.

The electrically conductive material of the pads may be gold or silver.

The pads may be formed by the superposition of at least two different metallic layers. They may also be formed by the superposition of a metallic layer integral with the support and an ultra thin layer (several nm thick) of a material enabling the attachment of chemical or biological species.

The surface of the support may be a surface of a material chosen among dielectric materials, semiconductor materials and metallic materials.

Advantageously, the microsensor or the nanosensor further comprises means making it possible to increase the sensitivity of the sensor. These means may comprise a thin metallic film directly deposited on said surface of the support. A thin dielectric film may be intercalated between the thin metallic film and the pads in order to adjust the plasmon resonance as a function of the thickness of the dielectric layer. These means may comprise a planar wave guide intended to convey a guided electromagnetic mode, said planar wave guide being formed on the surface or under the surface of the support and under the pads. They may be constituted by the grouping together of pads, the distance separating these grouped together pads being sufficiently small to allow an electromagnetic coupling between said grouped together pads. If the pads have a section in the shape of an ellipse, these means may be constituted by the small distance separating an end of a pad along the major axis of the ellipse from the end of the adjacent pad along the major axis of the ellipse, this small distance enabling an electromagnetic coupling between the pads.

The means making it possible to increase the sensitivity of the sensor may comprise at least one particle associated with a pad. This particle may be a particle fixed to said chemical or biological species. It may be fixed to an object intended to be placed near to a pad. This object may be the tip of a near field optical microscope. This particle may be metallic, the sensitivity is then reinforced by the coupling between the plasmon resonances of the pad and the particle. It may be constituted of a fluorescent material, the emission of fluorescence then being exacerbated by the plasmon resonance of the corresponding pad.

BRIEF DESCRIPTION OF DRAWINGS

The present invention will be better understood and other advantages and specific features will become more apparent on reading the description that follows, given by way of non-limiting illustration, taken in conjunction with the appended drawings, among which.

DETAILED DESCRIPTION OF SPECIFIC EMBODIMENTS

Figure 1:
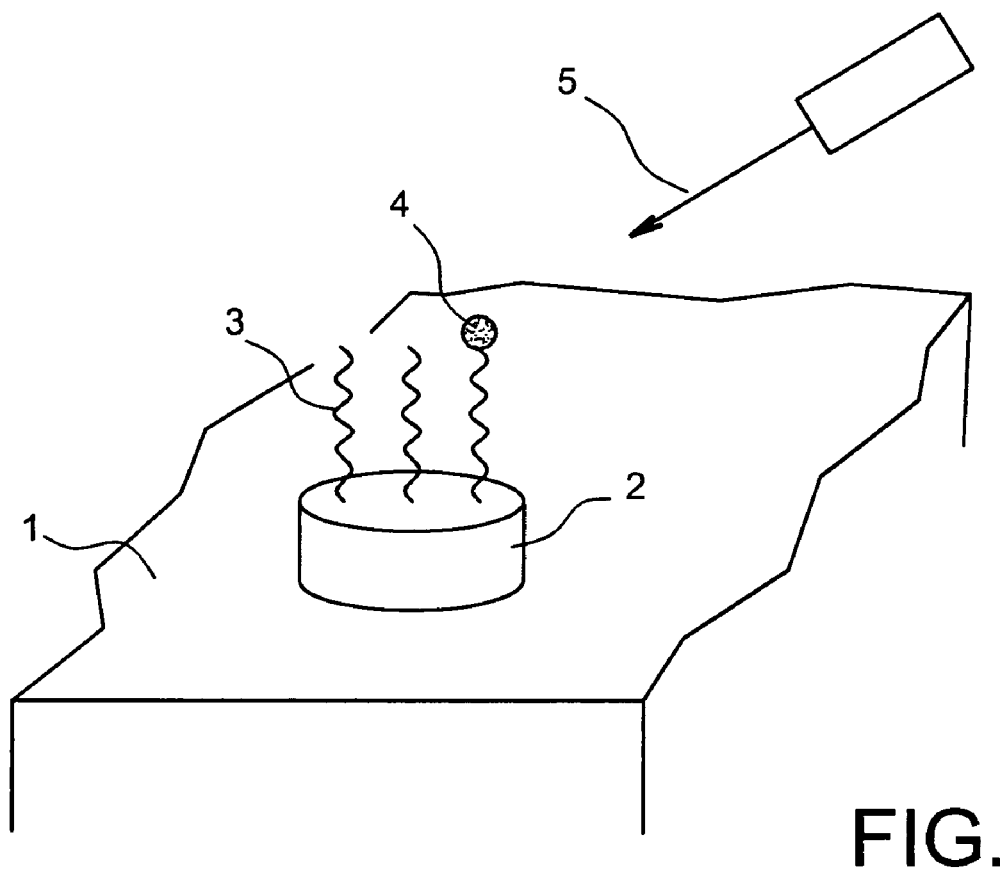
FIG. 1 is a view illustrating the operating principle of a microsensor or a nanosensor according to the invention.
Figure 2:
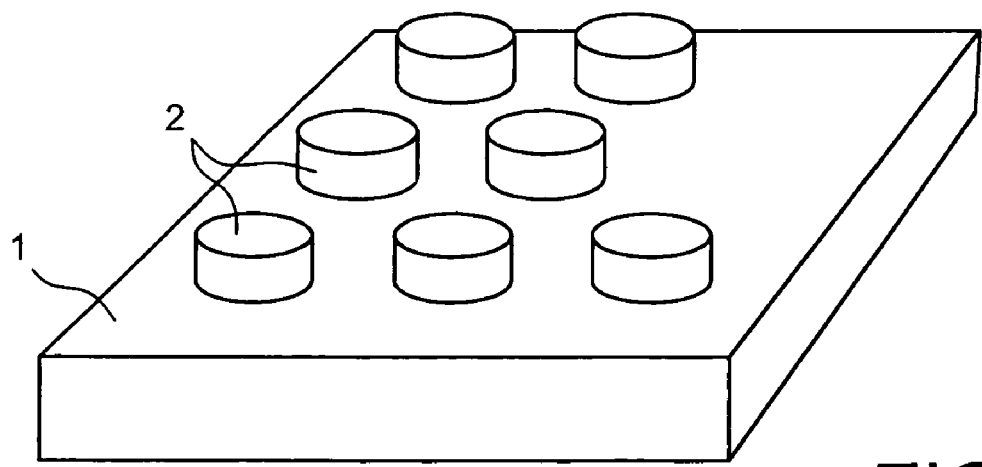
FIG. 2 is a perspective view of a microsensor or a nanosensor according to the present invention.

The invention will firstly be described in relation to FIGS. 1 and 2. FIG. 1 illustrates the operating principle of the invention whereas FIG. 2 is a perspective view of a sensor according to the present invention.

Metallic pads 2, for example in gold or in silver, are formed on the surface of a support 1. The support 1 may be of any nature: in dielectric material (for example in glass), semiconductor (for example in silicon) or metallic (for example a thin layer of gold deposited on a glass plate). The pads are distributed according to a two dimensional matrix. They are capable of adsorbing, on their upper face, chemical or biological species 3 such as strands of DNA.

In the case of a microsensor, the pads 2 may be cylindrical pads of 0.5 to 1 micrometer diameter, centre to centre separated by distances of around several µm to several hundreds of µm (for example from 5 µm to 300 µm). The thickness of the pads may be between 20 and 500 nm.

In the case of a nanosensor, the diameter of the pads is generally less than 0.5 µm and their centre to centre distance may be between 0.5 µm and 0.5 µm. The thickness of the pads may be between 10 nm and 100 nm.

The lighting 5 of the surfaces of the metallic pads to be studied and the detection of the optical signals coming from these pads are carried out either by a confocal optical microscope, however in a non-exclusive manner, preferentially in the case of pads of micronic size, or by a Scanning Near Field Optical Microscope (SNOM). Specific lighting parameters (polarisation, incidence angle, wavelength of the exciting light source) allow the surface plasmons to be excited at the scale of the pads.

For the lighting 5, one may envisage the possibility of creating a continuum of white light through non-linear effects (phase self-modulation, stimulated Raman effect) in an optic fibre from a femtosecond pulse laser source making it possible to have at one's disposal at the optic fibre output a source of white light in the visible spectrum, spatially confined and of sufficient intensity for the illumination of samples in a near field optical configuration. By way of non-limiting example, a titanium-sapphire laser, emitting pulses of 150 fs at a wavelength of 800 nm, may be coupled to a photonic crystal fibre of core diameter of 3 µm to create a continuum of white light of 200 mW power.

One may also envisage a lighting of the pads through a total reflection prism that makes it possible, through a lighting under evanescent wave, to increase the signal to noise ratio of the detection.

A wavelength analysis of each pad enables a plasmon signature of the pad concerned with or without adsorbed species. A reference spectrum is taken above a pad free of any adsorbed species. A second spectrum is taken after adsorption of species. The spectral shift between the two plasmon resonances makes it possible to detect the presence and the diversity of chemical or biological species adsorbed on each pad, and to evaluate their concentration. The study of the complete sample may be carried out either by a scanning of the light beam above the fixed sample or by a scanning of the sample under the fixed light beam. The excited Raman spectra obtained by a Raman spectroscopic analysis taken above each pad enable the identification of chemical species adsorbed on the pads.

Metallic particles 4 (FIG. 1), such as, by way of non-limiting example, spheres of gold or silver of several nanometers diameter, integral with certain biological or chemical species to be tested, may be used as markers. These particles 4 increase the sensitivity of the detection by reinforcing the plasmon resonance wavelength shift thanks to a coupling of the localised plasmons of these particles with those of the corresponding pads and by improving the signal to noise ratio of the detection.

By way of non-limiting example, a network of pads according to the invention is lithographed on a substrate of surface area of around $1 \times 1$ mm$^2$ comprising 10 000 cylindrical pads of sub-micronic diameter, 200 nm height, with 10 micrometer centre to centre spacing.

Figure 3:
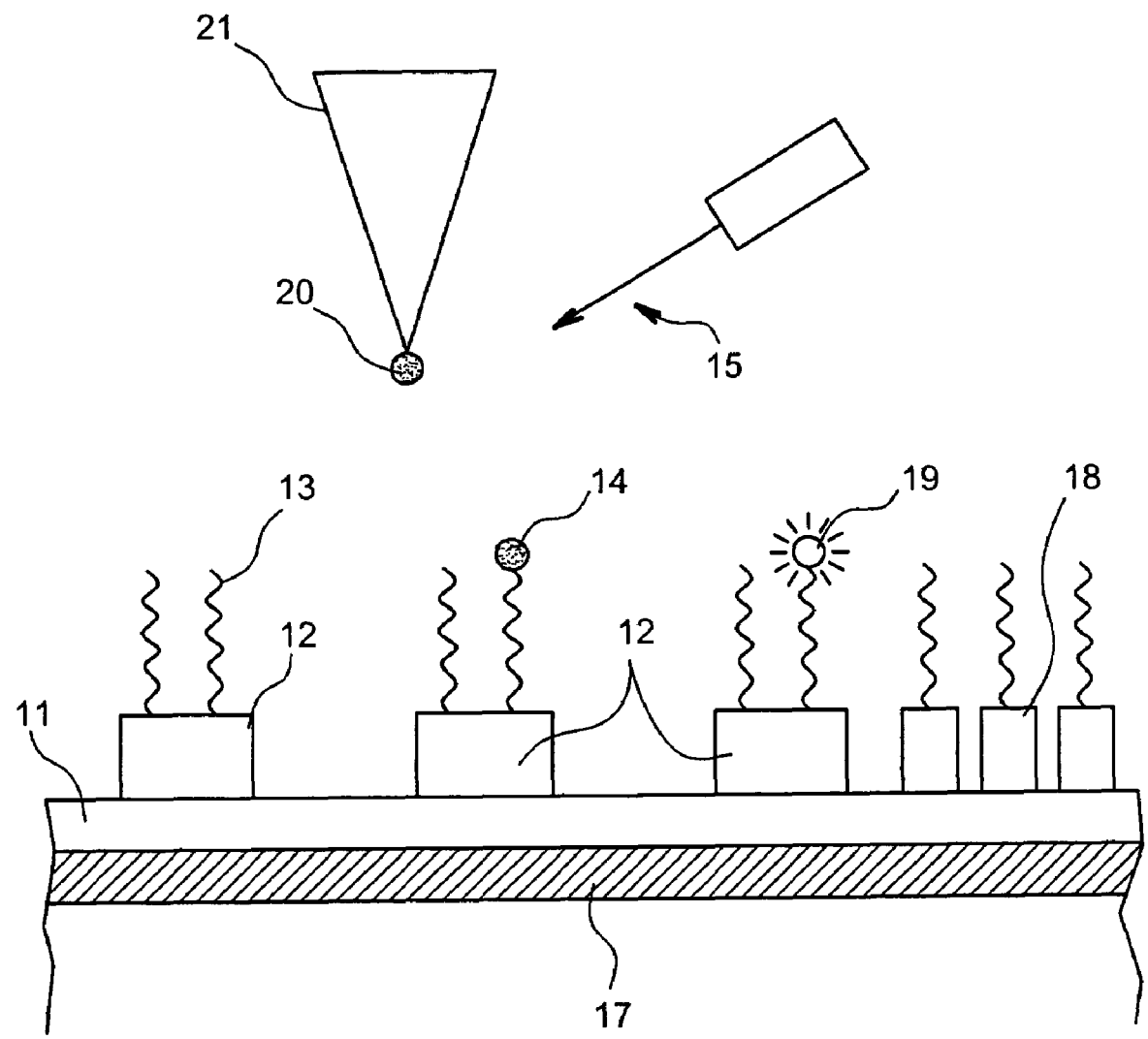
FIG. 3 is a view grouping together other embodiments of a nanosensor according to the present invention.

FIG. 3 is a view that groups together other embodiments of a nanosensor according to the present invention. It illustrates a localised surface plasmon sensor structure particularly suited to the sub-micronic characterisation of chemical or biological objects.

The nanosensor schematised in FIG. 3 is composed of a network of nanometallic pads 12 of very small dimensions formed on a substrate 11 and on which are absorbed the species 13 to be detected. By way of non-limiting example, the network of pads according to the invention is lithographed on a substrate of around $10 \times 10$ µm$^2$ surface area comprising 400 cylindrical pads of 50 nm diameter, 20 nm height with 500 nm centre to centre spacing.

Figure 4:
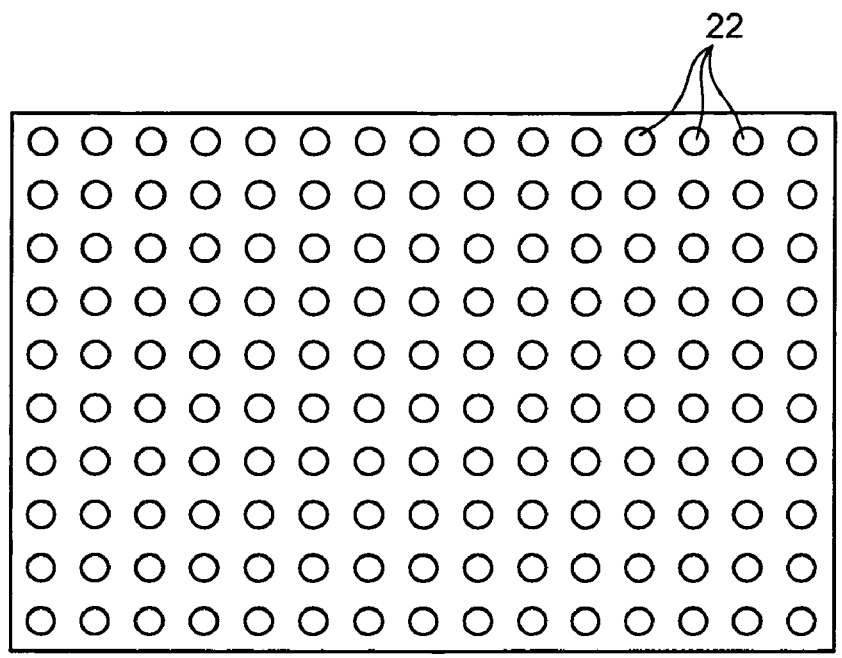
FIG. 4 is a top view of a microsensor or a nanosensor according to the present invention.
Figure 5:
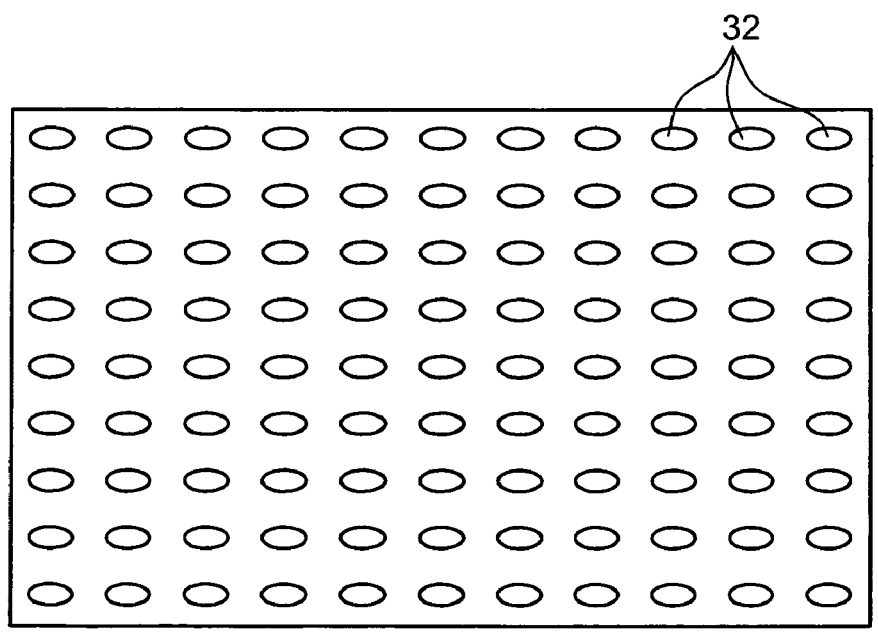
FIG. 5 is a top view of another microsensor or another nanosensor according to the present invention.

One preferentially uses, but by way of non-limiting example, nanopads 12 of cylindrical shape of circular or elliptic section, of typical dimension of several tens of nm (from 20 to 100 nm), of a height of 10 to 20 nm and spaced around 100 nm to 500 nm. These pads are preferentially formed by the technique of electronic lithography (pads in PMMA formed by exposure to electrons followed by a metallization, and finally a lift-off. FIGS. 4 and 5 respectively show a network of cylindrical pads (revolution cylinders) in gold 22 of diameter 100 nm and of height 70 nm, with 300 nm centre to centre spacing, and a network of pads of section in the shape of an ellipse, in gold 32 of height 50 nm, of major axis 65 nm and of minor axis 40 nm, with 150 nm spacings between minor axes and 200 nm spacings between major axes. It is possible to adjust the wavelengths of the plasmon resonances by modifying the size and/or the shape of the pads. The adjustment of this resonance wavelength to the exciting wavelength of a laser makes it possible to increase the sensitivity of detection in the case of an identification of biochemical species by surface enhanced Raman spectroscopy. The adjustment of the resonance wavelength of the pads to the (fluorescence) absorption or emission wavelength of fluorescent particles 19 (quantum boxes or organic molecules, by way of non-limiting example), playing the role of markers and further being able to be fixed to the biochemical species, also enables the fluorescence signal emitted by the markers to be increased.

The sensor may also be composed of several networks of particles of nanopads produced on a same substrate, each network having its own geometric characteristics. For example, by way of non-limiting example, the networks of FIGS. 4 and 5 may be formed on a same substrate. Thus each network will have its own plasmon signature at a defined wavelength. By way of non-limiting example, the resonance wavelength of each network may be adjusted to the wavelength of several lasers to identify the species by Raman spectroscopy or to the fluorescence absorption or emission wavelength of several markers.

The nanopads, of cylindrical shape (of section in the shape of a circle or an ellipse), by way of non-limiting example, may have a multilayer structure in order to enable the grafting of molecules that could not be directly grafted onto a metallic surface or in order to increase the sensitivity and/or the wavelength tunability of the sensor. In the first case, (grafting of molecules) for example, by way of non-limiting example, a cylindrical pad of 100 nm diameter may be composed of two layers, a lower layer of 50 nm of gold and an upper layer of 3 nm of silicon. In the second case (sensitivity and/or tunability), by way of non-limiting example, a cylindrical pad of 100 nm diameter may be composed of two metallic layers, a lower layer of 20 nm of silver and an upper layer of 10 nm of gold.

Metallic particles 14, by way of non-limiting example spheres of gold the diameter of which is typically several nm, may be attached to the chemical or biological species themselves to increase the sensitivity of the detection by coupling between the plasmon resonances of the pads 12 and those of the metallic particles.

The specific supports on which are deposited the pads may also increase the sensitivity of the sensor by couplings between the pads and guided electromagnetic mode. For example, by way of non-limiting example, metallic pads may be deposited on the surface of a planar or confined wave guide 17 or on a thin metallic film having resonances associated with the excitement of surface plasmons.

In order to increase the sensitivity of the sensor, the pattern of the network may be composed of several metallic sub-structures 18 (see FIG. 3) electromagnetically coupled between each other. This coupling reinforces the local electromagnetic field associated with the plasmon resonance and thereby the sensitivity of the detection. The closer together the sub-structures, the higher this coupling will be. It will also be higher for sub-structures in which the pads have sections in the shape of ellipses aligned along their major axis, thanks to the very intense fields created by point effect near to the low terminal bend radius of the major axis. For example, the pattern of the network may be composed of three coupled ellipse section nanopads 18, aligned along their major axis, of major axis 65 nm and of minor axis 40 nm, separated by several nm, by way of non-limiting example.

Other objects, fluorescent spherical particles (quantum boxes or spheres of latex doped with organic colorants for example) or fluorescent molecules 19, playing the role of markers, may also be fixed on the species and thereby make it possible to increase the sensitivity of the detection of the modification of the plasmon resonance of the pads when it is similar to the wavelength for which the absorption of the particles or molecules 19 is at a maximum. The perturbation of the plasmon resonance of the pad is higher in the presence of an absorbent species than in the presence of a non absorbent species.

The detection of the optical signal at the scale of nanometric pads, in other words at a sub-wavelength scale, is preferentially carried out by means of a confocal microscope if the distance between pads is greater than a micrometer (below this, the confocal is under the diffraction limit) and by means of a SNOM type scanning near field optical microscope if the distance between pads is less than a micrometer and by way of non-limiting example in an opening free probe configuration.

A metallic tip of the SNOM with probe without openings 21 under specific lighting conditions can bring about, by tip effect, an excitement of the electromagnetic field in the neighbourhood of said field thus reinforcing the luminous intensity near to the nano-objects to be detected. This tip further enables, through coupling of its plasmon resonance, if the material constituting this tip so allows, with that of the metallic nano-pad 12 and if appropriate that of a metallic marker 14, of even more marked wavelength resonance shifts of the system constituted by the tip, the pad and the marker, and therefore an improved sensitivity of the optical detection at sub-wavelength scale. The signal to noise ratio of the detection of the near field signal may be improved by vertically vibrating the probe above the sample. Thus, by means of a synchronous detection or a double gate photon counter, the confined evanescent fields in the vicinity of the pads, enabling the detection of the plasmon resonance with a high spatial resolution, are extracted from the background noise constituted by the diffusion coming from the illuminated surface. In the case of a synchronous detection the signal is demodulated at the vibration frequency of the probe. In the case of a double photon counter, a temporal gate is successively opened in the lower position and in the upper position of the vibration of the tip, the system then operating a subtraction of the two signals thus reinforcing the detection of confined fields.

According to another embodiment of the invention, one uses, as is shown in FIG. 3, a SNOM probe with opening (by way of non-limiting example) 21 at the end of which a metallic or fluorescent particle 20 of very small size (typically several nm) has been fixed. This particle, when it is fluorescent, may be, by way of non-limiting example, a molecule or a fluorescent quantum box and when it is metallic a sphere of gold or silver of several nm diameter.

This metallic particle 20 shows under an optical excitement 15 optical resonances linked to the excitement of localised surface plasmons. It ensures from this, in the vicinity of the particle 20 under the influence of the species 13 to be detected and to be characterised, a modification of the plasmon resonance of the particle 20 highlighted by the detection system of the SNOM.

The excitement of the electromagnetic field in the vicinity of the particle 20 may be reinforced by a coupling between the plasmon resonances of the particle 20, those of the cylindrical pads of section in the shape of a circle or an ellipse 12 or 18, if appropriate the resonances of the markers 14 and the guided electromagnetic mode 17.

In the case of a fluorescent particle, the presence of biochemical species modifies the intensity and the fluorescence lifetime of this particle. Thus, depending on the presence or not of the species 13 sought, the characteristics of the fluorescence radiation of the particle 20 are modified. The sensitivity of the fluorescence detection may be reinforced by the presence of pads 12 if the plasmon resonance wavelength of these pads is adjusted to the fluorescence absorption or emission wavelength of the particle 20. The fluorescent particle 20 may also be used to reinforce the modification of the plasmon resonance of the pads 12 induced by the species 13.

It should be noted that the invention may be exploited in liquid medium, in other words if the chemical or biological species are in a solution.

The invention claimed is:

1. A surface plasmon microsensor or nanosensor for chemical or biological species, comprising:
   metallic, cylindrical pads distributed on the surface of a support, the pads having a thickness between 10 nm and 500 nm and configured to immobilize the chemical or biological species, and the pads having a dimension, other than the thickness, that is less than 1 µm.

2. A microsensor or nanosensor according to claim 1, wherein the pads are distributed on the surface of the support according to a two-dimensional matrix.

3. A microsensor or nanosensor according to claim 1, wherein the pads have a section in a shape of a circle or an ellipse.

4. A microsensor according to claim 3, wherein the section of the pads has its largest dimension between 0.5 µm and 1 µm.

5. A microsensor or nanosensor according to claim 3, wherein the section of the pads has its largest dimension less than 0.5 µm.

6. A microsensor or nanosensor according to claim 1, comprising at least first and second networks of pads, a shape of a section of the pads of the first network being different from a shape of a section of pads of the second network.

7. A microsensor or nanosensor according to claim 1, wherein the pads include gold or silver.

8. A microsensor or nanosensor according to claim 1, wherein the pads are formed by superposition of at least two different metallic layers.

9. A microsensor or nanosensor according to claim 1, wherein the pads include a metallic layer integral with the support and an ultra thin layer of a material enabling attachment of the chemical or biological species.

10. A microsensor or nanosensor according to claim 1, wherein the surface of the support is a surface of a material chosen among dielectric materials, semiconductor materials, and metallic materials.

11. A microsensor or nanosensor according to claim 1, further comprising means for increasing sensitivity of the sensor.

12. A microsensor or nanosensor according to claim 11, wherein the means for increasing the sensitivity of the sensor includes a thin metallic film deposited on the surface of the support.

13. A microsensor or nanosensor according to claim 12, wherein a thin dielectric film is intercalated between the thin metallic film and the pads to adjust plasmon resonance as a function of thickness of the dielectric layer.

14. A microsensor or nanosensor according to claim 11, wherein the means for increasing the sensitivity of the sensor includes a planer wave guide configured to convey a guided electromagnetic mode, the planar wave guide being formed on the surface or under the surface of the support and under the pads.

15. A microsensor or nanosensor according to claim 11, wherein the means for increasing the sensitivity of the sensor is constituted by grouping together of pads, a distance separating the grouped together pads being sufficiently small to allow an electromagnetic coupling between the grouped together pads.

16. A microsensor or nanosensor according to claim 11, wherein the pads having a section in a form of an ellipse, and the means for increasing the sensitivity of the sensor is constituted by a small distance separating an end of a pad along the major axis of the ellipse from the end of the adjacent pad along the major axis of the ellipse, this small distance enabling an electromagnetic coupling between the pads.

17. A microsensor or nanosensor according to claim 11, wherein the means for increasing the sensitivity of the sensor includes at least one particle associated with a pad.

18. A microsensor or nanosensor according to claim 17, wherein the at least one particle is chosen from the group composed of metallic particles and fluorescent particles.

19. A microsensor or nanosensor according to claim 17, wherein the at least one particle is a particle fixed to the chemical or biological species.

20. A microsensor or nanosensor according to claim 17, wherein the at least one particle is fixed to an object intended to be placed near to a pad.

21. A microsensor or nanosensor according to claim 20, wherein the object is the tip of a near field optical microscope.

22. Use of the microsensor or the nanosensor according to claim 1 to carry out Raman spectroscopy at a level of detection by a reading system for identification of the chemical or biological species immobilized on the pads of the microsensor or the nanosensor.

23. A surface plasmon microsensor or nanosensor according to claim 1, wherein each of said pads has a surface that sustains surface plasmons at a first plasmon resonance wavelength when said chemical or biological species are not immobilized on said surface and sustains surface plasmons at a second plasmon resonance wavelength when said chemical or biological species are immobilized on said surface, wherein said first and second resonance wavelengths are shifted from each other by a detectable amount.

24. A surface plasmon microsensor or nanosensor according to claim 23, wherein said first and second resonance wavelengths are shifted by an amount detectable by Raman spectroscopy.

25. A surface plasmon microsensor or nanosensor according to claim 24, wherein said surface of each of said pads sustains localized surface plasmons at said first and second plasmon resonance wavelengths, wherein said localized surface plasmons propagate on said surface over distances less than a wavelength of a light exciting said localized surface plasmons on said surface.

26. A surface plasmon microsensor according to claim 1, wherein each of said pads has a diameter from 0.5 to 1 µm and a height from 20 to 500 nm, and wherein said pads have centers spaced from each other at a distance of 5 µm to 300 µm.

27. A surface plasmon nanosensor according to claim 1, wherein each of said pads has a diameter from 20 to 100 nm and a height from 10 to 20 nm, and wherein said pads are spaced from each other at a distance of 100 nm to 500 nm.

28. A surface plasmon microsensor or nanosensor according to claim 1, wherein a first plurality of said pads has a circular section and a second plurality of said pads has an elliptical section.

29. A surface plasmon microsensor or nanosensor according to claim 1, wherein a first plurality of said pads are geometrically configured so as to sustain surface plasmons at a first plasmon resonance wavelength when said chemical or biological species are immobilized on said pads of said first plurality, and a second plurality of said pads are geometrically configured so as to sustain surface plasmons at a second plasmon resonance wavelength when said chemical or biological species are immobilized on said pads of said second plurality, wherein said first and second plasmon resonance wavelengths are different from each other.

* * * * *